United States Patent [19]

Cimarusti et al.

[11] 4,443,374
[45] Apr. 17, 1984

[54] PROCESS FOR PREPARING (3S)-3-[[(2-AMINO-4-THIAZOLYL)[(1-CARBOXY-1-METHYLETHOXY)IMINO]ACETYL]AMINO]-2-OXO-1-AZETIDINESULFONIC ACID, AND 4-SUBSTITUTED DERIVATIVES

[75] Inventors: Christopher M. Cimarusti, Pennington; Rita T. Fox, Princeton; Alan W. Fritz, Kendall Park; William H. Koster, East Amwell Township, Hunterdon County; Jerome L. Moniot, Chester, all of N.J.

[73] Assignee: E. R. Squibb & Sons, Inc., Princeton, N.J.

[21] Appl. No.: 344,895

[22] Filed: Feb. 1, 1982

[51] Int. Cl.³ .............. C07D 417/12; C07D 205/08; A61K 31/425
[52] U.S. Cl. ..................... 260/245.4; 260/239 A
[58] Field of Search ................... 260/239 A, 245.4

[56] References Cited

U.S. PATENT DOCUMENTS

| | | | |
|---|---|---|---|
| 4,024,133 | 5/1977 | Cook et al. | 424/246 |
| 4,166,115 | 8/1979 | Takaya | 544/30 |
| 4,191,762 | 3/1980 | Kamiya et al. | 544/16 |
| 4,201,779 | 5/1980 | Bormann et al. | 544/21 |
| 4,225,707 | 9/1980 | Kamiya et al. | 546/16 |

FOREIGN PATENT DOCUMENTS

| | | |
|---|---|---|
| 30630 | 6/1981 | European Pat. Off. |
| 2822861 | 11/1979 | Fed. Rep. of Germany |
| 3239157 | 5/1983 | Fed. Rep. of Germany |
| 1389194 | 4/1975 | United Kingdom |

OTHER PUBLICATIONS

Georgopapadakou et al., European J. Biochem. 124, 507, (1982).

Primary Examiner—Mark L. Berch
Attorney, Agent, or Firm—Lawrence S. Levinson; Donald J. Barrack

[57] ABSTRACT

Disclosed herein is a process for preparing a compound having the formula

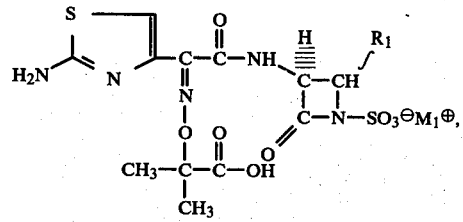

which comprises coupling a compound having the formula

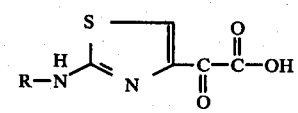

or a salt thereof, with a compound having the formula

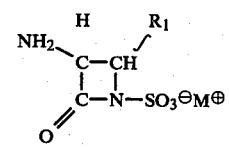

to obtain a compound having the formula

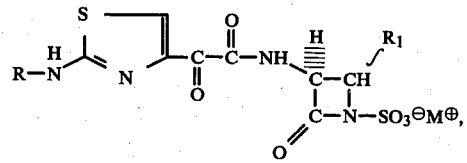

reacting that compound with 2-aminooxy-2-methylpropanoic acid, or a salt thereof, to obtain a compound having the formula

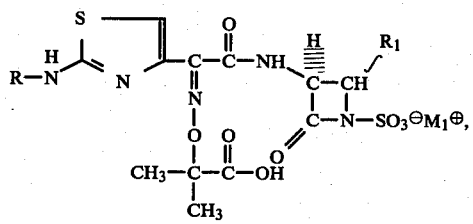

and, if R is an amino protecting group, deprotecting that compound to yield the desired product; wherein R is hydrogen or an amino protecting group;
$R_1$ is hydrogen, methyl or ethyl;
$M^\oplus$ is an inorganic cation or a substituted ammonium ion; and
$M_1^\oplus$ is hydrogen, an inorganic cation or a substituted ammonium ion.

4 Claims, No Drawings

PROCESS FOR PREPARING (3S)-3-[[(2-AMINO-4-THIAZOLYL)[(1-CARBOXY-1-METHYLETHOXY)IMINO]-ACETYL]AMINO]-2-OXO-1-AZETIDINESULFONIC ACID, AND 4-SUBSTITUTED DERIVATIVES

BACKGROUND OF THE INVENTION

U.K. patent application No. 2,071,650, published Sept. 23, 1981, discloses β-lactam antibiotics including (3S)-3-[[(2-amino-4-thiazolyl)[(1-carboxy-1-methylethoxy)imino]acetyl]amino]-2-oxo-1-azetidinesulfonic acid, and 4-substituted derivatives thereof.

BRIEF DESCRIPTION OF THE INVENTION

This invention is directed to a process for the preparation of (3S)-3-[[(2-amino-4-thiazolyl)[(1-carboxy-1-methylethoxy)imino]acetyl]amino]-2-oxo-1-azetidinesulfonic acid and 4-substituted derivatives thereof. The process of this invention can be represented diagrammatically as follows:

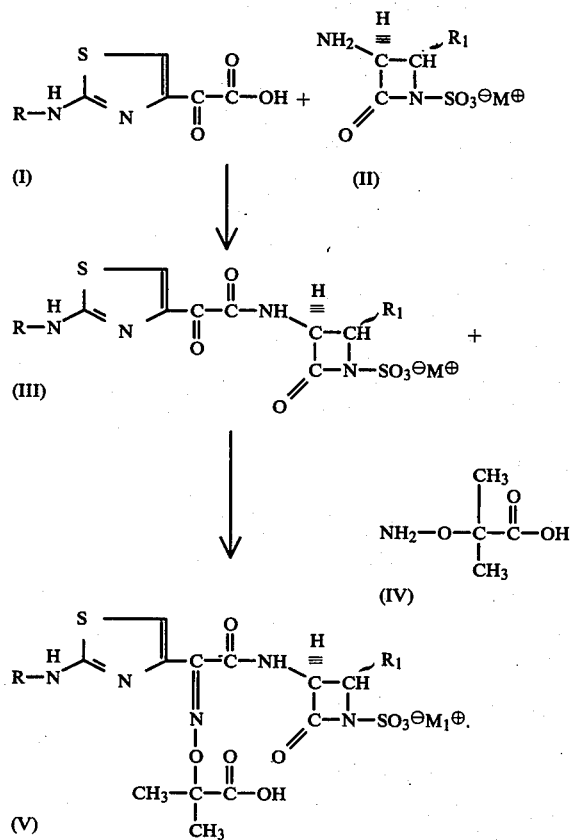

In the above formulas, and throughout the specification, the symbols are as defined below.

R is hydrogen or an amino protecting group;
$R_1$ is hydrogen, methyl or ethyl;
$M^\oplus$ is an inorganic cation or a substituted ammonium ion; and
$M_1^\oplus$ is hydrogen, an inorganic cation, or a substituted ammonium ion.

The term "amino protecting group" refers to any group which will protect the nitrogen atom to which it is attached from reacting in the above sequence, and which, at the end of the above-described reaction sequence, can be cleaved from the nitrogen atom under conditions that do not alter the rest of the molecule. Exemplary amino protecting groups are triphenylmethyl, formyl, t-butoxycarbonyl, benzyloxycarbonyl, 1,1-dimethylpropoxycarbonyl, or

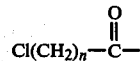

wherein n is 1 or 4.

The term "inorganic cation" refers to any positively charged inorganic atom or group of atoms. Exemplary inorganic cations are the alkali metals (e.g., lithium, sodium and potassium), the alkaline earth metals (e.g., calcium and magnesium), and ammonium ($NH_4^\oplus$).

The term "substituted ammonium ion" refers to organic cations; the tri- and tetra-substituted ammonium ions are specifically contemplated. Exemplary substituted ammonium ions are the pyridinium, triethylammonium, and tetrabutylammonium salts.

DETAILED DESCRIPTION OF THE INVENTION

The process of this invention yields compounds of formula V. Those compounds of formula V wherein R is other than hydrogen can be deprotected to yield the corresponding compound of formula V wherein R is hydrogen. As described in U.K. patent application No. 2,071,650, published Sept. 23, 1981, compounds of formula V are β-lactam antibiotics useful for combating bacterial infections (including urinary tract infections and respiratory infections) in mammalian species, such as domesticated animals and humans. It is further disclosed that for combating bacterial infections in mammals, a compound of formula V can be administered to a mammal in need thereof in an amount of about 1.4 mg/kg/day to about 350 mg/kg/day, preferably about 14 mg/kg/day to about 100 mg/kg/day.

The reaction of an aminothiazolylglyoxylic acid of formula I, or a salt thereof, and a (3S)-3-amino-2-oxo-1-azetidinesulfonic acid salt of formula II proceeds most readily if the aminothiazolylglyoxylic acid is in an activated form. Activated forms of carboxylic acids are well known in the art and include acid halides, acid anhydrides (including mixed acid anhydrides), activated acid amides and activated acid esters. The preferred activated form of a glyoxylic acid of formula I for use in the process of this invention is the mixed acid anhydride with diphenylphosphinic acid or 2,2-dimethylpropanoic acid. Mixed acid anhydrides for use in the process of this invention can also be formed from a glyoxylic acid of formula I and a substituted phosphoric acid (such as diphenylphosphoric acid, dialkylphosphoric acid, dialkoxyphosphoric acid, diphenoxyphosphoric acid, or dibenzylphosphoric acid), dialkylphosphorous acid, sulfurous acid, thiosulfuric acid, sulfuric acid and others. Exemplary of the activated amides which can be used in the process of this invention are those formed from a glyoxylic acid of formula I and imidazole, 4-substituted imidazoles, dimethylpyrazole, triazole, tetrazole or dimethylaminopyridine. Exemplary of the activated esters which can be used in the process of this invention are the cyanomethyl, methoxymethyl, dimethyliminomethyl, vinyl, propargyl, 4-nitrophenyl, 2,4-dinitrophenyl, trichlorophenyl, pentachlorophenyl, mesylphenyl, phenylazophenyl, phenylthio, 4-nitrophenylthio, p-cresylthio, carboxymethylthio, pryanyl, pyridyl, piperidyl, and 8-quinolylthio esters. Additional examples of activated esters are esters with an N-hydroxy compound such as N,N-dimethylhydroxylamine, 1-hydroxy-2(1H)pyridone, N-hydroxysuccinimide, N-hydroxyphthalimide, and 1-hydroxy-6-chloro-1H-benzotriazole.

The ketoamides of formula III, which result from the coupling of an aminothiazolylglyoxylic acid of formula I (or a salt thereof) and a (3S)-3-amino-2-oxo-1-azetidinesulfonic acid salt of formula II can be condensed in water, or in an organic solvent, with 2-aminooxy-2-methylpropanoic acid, or a salt thereof, selectively yielding the corresponding syn-oxime of formula V. If the pH of the condensation reaction mixture is far to the acid side (i.e., about 2.5 or less), the syn-oxime of formula V will be in the form of the zwitterion (i.e., $M_1^\oplus$ is hydrogen). If the pH of the condensation reaction mixture is more than about 3.2, the syn-oxime of the formula V will be a salt corresponding to the salt of formula III (i.e., $M_1^\oplus$ in formula V is the same as $M^\oplus$ in formula III).

The following examples are specific embodiments of this invention.

EXAMPLE 1

[3S-[3α(Z),4β]]-3-[[(2-Amino-4-thiazolyl)[(1-carboxy-1-methylethoxy)imino]acetyl]amino]-4-methyl-2-oxo-1-azetidinesulfonic acid Preparation Using (2-Amino-4-Thiazolyl)glyoxylic Acid (A) (2-Amino-4-thiazolyl)glyoxylic acid

[2-(Formylamino)-4-thiazolyl]glyoxylic acid (10 g, 0.05 mol) suspended in methanol (100 ml) was combined with concentrated hydrochloric acid (6.25 ml, 0.075 mol) and stirred overnight at room temperature causing dissolution of the solid. After filtration to remove a small amount of insoluble material, solvent was removed in vacuo. The residue was suspended in water and the pH was adjusted to 2 with potassium hydroxide solution. The solid was collected by filtration, washed with water, then twice with acetone, followed by two washings with ether, giving 4.21 g of a powder.

A second crop was obtained by concentrating the filtrate, lowering the pH to 0.8, and collecting and washing as above to obtain 3.74 g of a powder.

Both crops were the hydrochloride salt of the title compound. They were dissolved in water at pH 7–8, the pH was then lowered to pH 3.1–3.3, the precipitate was collected, washed twice with acetone, then twice with ether yielding 5.96 g of the title compound.

(B) (2-Amino-4-thiazolyl)glyoxylic acid, triethylamine salt

To (2-amino-4-thiazolyl)glyoxylic acid suspended in methanol (50 ml) was added triethylamine (5.3 ml), causing the solid to dissolve. After filtration, solvent was removed in vacuo and the crystalline residue was triturated with acetone, then ether, and dried in vacuo (8.13 g; product slowly melts with decomposition over a broad range).

Anal. Calc'd for $C_{11}H_{19}N_3O_3S$ (273.38): C, 48.33; H, 7.01; N, 15.37; S, 11.73. Found: C, 48.02; H, 7.12; N, 15.26; S, 11.43.

(C) (3S-trans)-3-[[(2-Amino-4-thiazolyl)oxoacetyl]amino]-4-methyl-2-oxo-1-azetidinesulfonic acid, potassium salt To a solution of diphenylphosphinyl chloride (1.85 g, 7.82 mmol) in dry dimethylformamide (15 ml) cooled in an ice-methanol bath (−15° to −20° C.) was added (2-amino-4-thiazolyl)glyoxylic acid, triethylamine salt (2.14 g, 7.82 mmol). After stirring for ½ hour a solution of (3S-trans)-3-amino-4-methyl-2-oxo-1-azetidinesulfonic acid, triethylamine salt (1.08 g, 6 mmol) and triethylamine (1.92 ml, 13.8 ml) in dry dimethylformamide (5 ml) was added to the cold mixed anhydride solution and the reaction mixture was stirred at 5° C. for 24 hours. Solvent was removed in vacuo, the residual oil was dissolved in water, and chromatographed on Dowex 50 X 2-400 mesh resin ($K^\oplus$ form, 200 ml, 0.7 meq/ml). Upon elution with water (15 ml fractions) the crude product was collected in fractions 13–27 (3.37 g). Chromatography on HP-20 resin (200 ml), eluting with water (15 ml fractions), gave the title compound in fractions 18–26. Removal of water in vacuo gave the title compound as an amorphous powder.

Anal. Calc'd For $C_9H_9N_4O_6S_2K$ (372.42): C, 29.02; H, 2.44; N, 15.04; S, 17.22; K, 10.50. Found: C, 28.87; H, 2.62; N, 14.85; S, 16.88; K, 10.81.

(D) [3S-[3α(Z),4β]]-3-[[(2-Amino-4-thiazolyl)-[(1-carboxy-1-methylethoxy)imino]acetyl]amino]-4-methyl-2-oxo-1-azetidinesulfonic acid Method I (3S-trans)-3-[[(2-Amino-4-thiazolyl)oxoacetyl]amino]-4-methyl-2-oxo-1-azetidinesulfonic acid, potassium salt (33 mg, 0.1 mmol) was dissolved in water (0.3 ml) together with 2aminooxy-2-methylpropanoic acid (12 mg, 0.1 mmol) and the mixture was allowed to stand for 48 hours at room temperature. Lowering the pH to 1.9 with 6 N hydrochloric acid caused the product to crystallize. The product was washed with cold water followed by acetone, yielding 17 mg of product as a solid.

Method II

The procedure of Method I was repeated using 23 mg (0.1 mmol) of the trifluoroacetate salt of 2-aminooxy-2-methylpropanoic acid. The desired product precipitated from solution, and after cooling, was collected and dried.

Method III (3S-trans)-3-[[(2-Amino-4-thiazolyl)(oxoacetyl]amino]-4-methyl-2-oxo-1-azetidinesulfonic acid, potassium salt (50 mg, 0.15 mmol) and 2-aminooxy-2-methylpropanoic acid (18 mg, 0.15 mmol) were dissolved in 0.5 M pH 5.8 phosphate buffer and stirred at room temperature for 24 hours. After standing for 24 hours at 5° C., the pH was lowered to 2 with 1 N hydrochloric acid and the solution was concentrated under a stream of nitrogen. After cooling at 5° C., crystals were collected from the concentrated solution, washed with cold water, then with acetone-ether, and dried to give 30 mg of product as a powder.

Method IV (3S-trans)-3-[[(2-Amino-4-thiazolyl)oxoacetyl]amino]-4-methyl-2-oxo-1-azetidinesulfonic acid, potassium salt (25 mg, 0.067 mmol) and 2-aminooxy-2-methylpropanoic acid (9 mg, 0.076 mmol) dissolved in water (0.3 ml) were heated to 60° C. After 2 hours the mixture was cooled, the pH was lowered to 1.8 with 1 N hydrochloric acid, and after standing at 5° C. the crystallized product was collected. Washing with acetone-ether and drying gave 14 mg of product as a powder.

Method V (3S-trans)-3-[[(2-Amino-4-thiazolyl)oxoacetyl]amino]-4-methyl-2-oxo-1-azetidinesulfonic acid, potassium salt (50 mg, 0.134 mmol) and 2-aminooxy-2- methylpropanoic acid (105 mg, 0.450 mmol) were dissolved in dimethylformamide (1 ml) and stirred at room temperature for 24 hours. Solvent was removed in vacuo and residue was crystallized from water on cooling. The solid was collected and washed with cold water, then with acetone-ether, and dried to give 27 mg of product as a powder.

Preparation Using
[2-(Formylamino)-4-Thiazolyl]glyoxylic Acid (A) (3S-trans)-3-[[[2-(Formylamino)-4-thiazolyl]oxoacetyl]amino]-4-methyl-2-oxo-1-azetidinesulfonic acid, potassium salt Method I (non-aqueous procedure)

Trimethyl acetyl chloride (3.7 ml, 0.03 mole) was added to a solution of 2.42 ml (0.03 mole) of pyridine in 25 ml of acetonitrile at −30° C. The solution was stirred for 5 minutes. A precooled (−15° C.) solution of 5.0 g (0.025 mole) of [2-(formylamino)-4-thiazolyl]glyoxylic acid and 4.2 ml (0.03 mole) of triethylamine in 25 ml of acetonitrile was added over 1 to 2 minutes at a rate to keep the reaction temperature below −20° C. The mixture was stirred for 5 minutes at −25° C., and then a precooled (−15° C.) solution of 4.26 g (0.024 mole) of (3S-trans)-3-amino-4-methyl-2-oxo-1-azetidinesulfonic acid and 3.72 ml (0.027 mole) of triethylamine in 30 ml of acetonitrile were added. The mixture was stirred for 1 hour at −25° C.±2. The mixture was filtered through Celite and the Celite was washed with 80 ml of acetonitrile. The combined filtrate was treated with 25 ml of 1.9 mole aqueous potassium acetate and stirred for 10 minutes. The mixture was diluted with 50 ml of isopropanol and filtered. The solid was washed (isopropanol, acetone) and dried in vacuo at room temperature to give the crude product, 9.16 g. Diluting the filtrate with 200 ml of isopropanol gave a second crop of crude product, 0.22 g.

Method II (non-aqueous procedure)

Trimethyl acetyl chloride, (3.7 ml, 0.03 mole) was added to a solution of 2.42 ml of (0.03 mole) of pyridine in 25 ml of acetonitrile at −16° C. The solution was stirred 5 minutes. A precooled (−15° C.) solution of 5.0 g (0.025 mole) of [2-(formylamino)-4-thiazolyl]glyoxylic acid and 4.2 ml (0.03 mole) of triethylamine in 25 ml of acetonitrile was added over 1 to 2 minutes at a rate to keep the reaction temperature below −9° C. The mixture was stirred for 5 minutes at −15° C., and then a precooled (−15° C.) solution of 4.26 g (0.024 mole) of (3S-trans)-3-amino-4-methyl-2-oxo-1-azetidinesulfonic acid and 3.72 ml (0.027 mole) of triethylamine in 30 ml of acetonitrile was added. The mixture was stirred for 1 hour at −13° C.±2°. The mixture was filtered through Celite and the Celite was washed with 80 ml of acetonitrile. The combined filtrate was treated with 25 ml of 1.9 molar aqueous potassium acetate and stirred for 10 minutes. The mixture was diluted with 50 ml of isopropanol and filtered. The solid was washed (isopropanol), acetone) and dried in vacuo at room temperature to give the crude product, 7.0 g. Diluting the filtrate with 200 ml of isopropanol gave a second crop of crude product, 1.22 g.

Method III (aqueous procedure)

A precooled (−10° C.) solution of 4.96 ml (0.04 mole) of trimethyl acetyl chloride in 40 ml of acetonitrile was added over 1 to 2 minutes to a precooled (−17° C.) solution of 8.0 g (0.04 mole) of [2-(formylamino)-4-thiazolyl]glyoxylic acid and 6 ml (0.04 mole) of triethylamine in 40 ml of acetonitrile; the mixture was stirred for 5 minutes. A precooled (−10° C.) solution of 5 g (0.026 mole) of (3S-trans)-3-amino-4-methyl-2-oxo-1-azetidinesulfonic acid, 3.87 ml (0.028 mole) of triethylamine and 2.24 ml (0.028 mole) of pyridine in 80 ml of 1:1 water-acetonitrile was added over 1 to 2 minutes and the mixture was stirred for 30 minutes at −15° C. The mixture was diluted with 350 ml of pH 4.5 phosphate buffer and extracted with ethyl acetate. The aqueous layer was filtered through Celite; the filtrate was treated with a solution of 9.4 g (0.028 mole) of tetrabutylammonium hydrogen sulfate and 28 ml of 1.0 N aqueous potassium bicarbonate in 50 ml of water. The aqueous solution was extracted with dichloromethane (five 350 ml) portions. The dichloromethane solution was dried over sodium sulfate, filtered, and the filtrate evaporated in vacuo to give 13.7 g of a foam residue. This material was dissolved in 300 ml of isopropanol and 23 ml of 1 N aqueous potassium acetate was added. The solid which precipitated was collected, washed (isopropanol and acetone), and dried in vacuo at room temperature to give the crude product, 8.24 g.

Method IV (non-aqueous procedure)

To a solution of pyridine (40.25 ml) in dichloromethane (625 ml) at −35° C. under an inert atmosphere was added a precooled (−25° C.) solution of pivaloyl chloride (61.5 ml) in methylene chloride (65 ml) at a rate to maintain the internal temperature below −25° C. After two minutes of stirring, a precooled (−25° C.) solution of [2-(formylamino)-4-thiazolyl]glyoxylic acid (100 g) and triethylamine (70 ml) in methylene chloride (200 ml) was added at a rate to maintain internal reaction temperature below −25° C. After stirring for two minutes, a precooled (−15° C.) solution of (3S-trans)-3-amino-4-methyl-2-oxo-1-azetidinesulfonic acid (90 gm) and triethylamine (70 ml) in acetonitrile (250 ml) was added at a rate to maintain the internal reaction temperature below −25° C. and the mixture was stirred at −25° C.±3° C. for about 1 hour. The mixture was diluted with 1.5 liters of acetonitrile and the dichloromethane was removed in vacuo. The acetonitrile solution was stirred vigorously and treated with 2 M aqueous potassium acetate (500 ml). After 10 minutes, the solution was diluted with isopropanol (2.5 liters) and stirred for 20 minutes. The solids were collected by filtration, washed with acetonitrile and ethanol, air dried and dried in vacuo (1 mm Hg) at 50° C. for 4 hours, and at 25° C. for 12 hours to give 0.23 kg of the title compound (purity by quantitative analysis 81%).

(B) [3S-[3α(Z),4β]]-3-[[[2-(Formylamino)-4-thiazolyl][(1-carboxy-1-methylethoxy)imino]-acetyl]amino]-4-methyl-2-oxo-1-azetidinesulfonic acid A solution of 2.33 g (10.0 mmole) of 2-aminooxy-2-methylpropanoic acid, trifluoroacetate salt, in 5 ml of water was made. The pH of this solution was adjusted from 0.5 to 2 with aqueous saturated potassium bicarbonate, then brought to 10 ml total volume with water. To this solution was added a 10 ml aqueous suspension of 2.0 g (5.0 mmole) of (3S-trans)-3-[[[2-(formylamino)-4-thiazolyl]oxoacetyl]amino]-4-methyl-2-oxo-1-azetidinesulfonic acid, potassium salt. The suspension was stirred at ambient temperature, (ca. 20°–25° C.); the pH was maintained at 2 by dropwise addition of saturated aqueous potassium bicarbonate. The suspension became a nearly clear solution after 5 hours. The solution was stirred for one additional hour, then filtered, and the filtrate lyophilized overnight. Crude lyophilate was used directly in the next step. Thin layer chromatography of the crude lyophilate showed the title compound to be the major product, the non-formylated analog as a by-product, and a more polar product.

(C) [3S-[3α(Z),4β]]-3-[[(2-Amino-4-thiazolyl)[(1-carboxy-1-methylethoxy)imino]acetyl]amino]-4-methyl-2-oxo-1-azetidinesulfonic acid Method I A solution of 4.3 ml of 2 N hydrochloric acid was made by adding 0.71 ml of concentrated hydrochloric acid (ca. 12 N) to 3.6 ml of water. To this solution was added 1.94 g (2.15 mmole) of crude lyophilate containing [3S-[3α(Z),4β]]-3-[[[2-(formylamino)-4-thiazolyl][(1-carboxy-1-methylethoxy)imino]acetyl]amino]-4-methyl-2-oxo-1-azetidinesulfonic acid. The solution was stirred at ambient temperature and in 90 minutes a precipitate formed. Stirring was continued for an additional 6 hours, and the reaction solution was diluted with 4 ml of isopropanol and filtered. The first filtrate was separated and the first crop was washed with 10 ml of isopropanol and 30 ml of ethyl acetate, and dried in vacuo at ambient temperature overnight, yielding 0.587 g of solid. Quantitative analysis versus standard showed it contained 81% of the desired product.

The first crop filtrate was diluted with a second 4 ml portion of isopropanol and stored at 0°–5° C. overnight. A second crop of product was collected by filtration and washed with isopropanol and ethyl acetate, then dried in vacuo at ambient temperature for 3 to 4 hours. A solid weighing 0.207 g was obtained. Quantitative analysis versus standard showed it contained 36.2% of the desired product.

Method II

To a solution of 2-aminooxy-2-methylpropanoic acid hydrochloride salt (0.186 kg) in water (1.5 liters) and acetonitrile (1.5 liters), preadjusted to pH 2.0 to 2.2 by addition of triethylamine, was added (3S-trans)-3-[[[2-(formylamino)-4-thiazolyl]oxoacetyl]amino]-4-methyl-2-oxo-1-azetidinesulfonic acid, potassium salt (see example 1A, 0.278 kg) in two equal portions and the suspension was stirred at 20° C. for 8 hours while the pH was maintained at pH 2.0–2.2 by further addition of triethylamine. To the resulting clear solution was added concentrated hydrochloric acid (216 ml) with vigorous stirring which was continued for 12 hours at 20° C. The resulting slurry was adjusted to pH 3.5–4.0 by the addition of saturated aqueous potassium bicarbonate and extracted with dichloromethane (3 liters). The aqueous layer was then treated with 3 liters of aqueous tetrabutylammonium hydrogen sulfate (0.7 kg), adjusted to pH 3.5 with saturated aqueous potassium bicarbonate, and the aqueous layer extracted with dichloromethane (6 liters). The dichloromethane layer was dried over sodium sulfate, filtered and treated dropwise with 97% formic acid (345 ml) and stirred at 20° C. for 40 minutes. The solids were collected by filtration, washed with methylene chloride and dried in vacuo for 4 hours at 50° C. and for 12 hours at 25° C. to give 0.25 kg of the title compound as a fine white crystalline powder. (Molar yield by quantitation vs standard=69%).

EXAMPLE 2

(3S)-3-[[(2-Amino-4-thiazolyl)[(1-carboxy-1-methylethoxy)imino]acetyl]amino]-2-oxo-1-azetidinesulfonic acid, sodium salt (A) (3S)-3-[[(2-Amino-4-thiazolyl)oxoacetyl]amino]-2-oxo-1-azetidinesulfonic acid, potassium salt To a solution of diphenylphosphinyl chloride (157 mg, 0.663 mmol) in dry dimethylformamide (1.5 ml), cooled to −15° to −20° C. in an ice-methanol bath, was added (2-amino-4-thiazolyl)glyoxylic acid, ethyldiisopropylamine salt (200 mg, 0.663 mmol). After stirring for 15 minutes, (3S)-3-amino-2-oxo-1-azetidinesulfonic acid (100 mg, 0.60 mmol) was added, followed by dimethylformamide (1 ml) and triethylamine (175 μl, 1.26 mmol). After stirring at 5° C. for 17 hours, solvent was removed in vacuo, the residual oil was dissolved in water, and chromatographed on an ion-exchange column (10 ml, Dowex 50 X 2–400, K⊕ form) eluting with water. The crude product, obtained as an oil, was dissolved in water and the addition of methanol caused a precipitate to form. The solid was collected by filtration and extracted several times with methanol. Solvent was removed from the combined filtrate and methanolic extracts and the residue was chromatographed on HP-200 resin (140 ml). The product was eluted with water and obtained as a yellow oil (90 mg).

(B) (3S)-3-[[(2-Amino-4-thiazolyl)[(1-carboxy-1-methylethoxy)imino]acetyl]amino]-2-oxo-1-azetidinesulfonic acid, sodium salt To a solution of (3S)-3-[[(2-amino-4-thiazolyl)oxoacetyl]amino]-2-oxo-1-azetidinesulfonic acid, potassium salt (90 mg, 0.251 mmol) in water (2 ml) was added 2-aminooxy-2-methylpropanoic acid, trifluoroacetate salt (117 mg, 0.503 mmol) and sodium acetate (62 mg, 0.75 mmol). The mixture (pH 4.2) was stirred at room temperature overnight. The pH was then raised to 6.7 with 0.5 N sodium hydroxide, and solvent was removed in vacuo. The crude product was chromatographed on HP-20 resin yielding the title compound (52 mg).

What is claimed is:

1. A process for preparing a compound having the formula

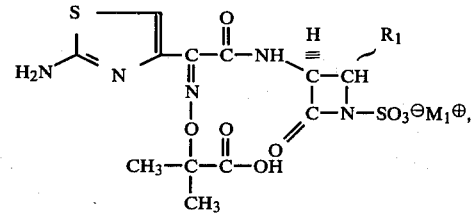

which comprises coupling a compound having the formula

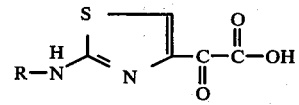

or a salt thereof, with a compound having the formula

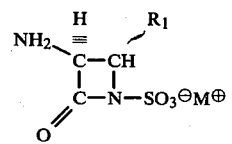

to obtain a compound having the formula

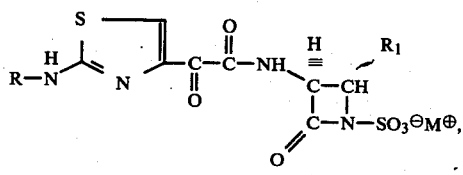

reacting that compound with 2-aminooxy-2-methyl-propanoic acid, or a salt thereof, to obtain a compound having the formula

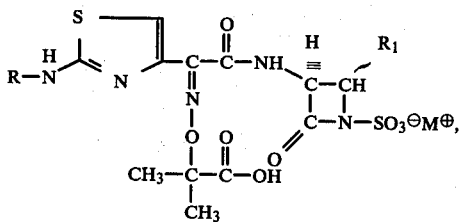

and, if R is an amino protecting group, deprotecting that compound to yield the desired product; wherein
R is hydrogen or an amino protecting group
$R_1$ is hydrogen, methyl or ethyl;
$M^\oplus$ is an inorganic cation or a pyridinium, triethylammonium, or tetrabutylammonium ion; and
$M_1^\oplus$ is the same as $M^\oplus$ or hydrogen.

2. A process in accordance with claim 1 wherein $R_1$ is α-methyl.

3. A process in accordance with claim 2 wherein R is hydrogen.

4. A process in accordance with claim 2 wherein R is formyl.

* * * * *